(12) United States Patent  
Liu et al.

(10) Patent No.: US 7,908,095 B2  
(45) Date of Patent: Mar. 15, 2011

(54) DETECTING DAMAGE IN METAL STRUCTURES WITH STRUCTURAL HEALTH MONITORING SYSTEMS

(75) Inventors: Paul B. Liu, Cupertino, CA (US); Fu-Kuo Chang, Stanford, CA (US); Shawn J. Beard, Livermore, CA (US); Irene Li, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 332 days.

(21) Appl. No.: 12/102,767

(22) Filed: Apr. 14, 2008

(65) Prior Publication Data  
US 2008/0255778 A1 Oct. 16, 2008

Related U.S. Application Data

(60) Provisional application No. 60/912,112, filed on Apr. 16, 2007.

(51) Int. Cl.  
*G06F 19/00* (2006.01)

(52) U.S. Cl. .......................................................... 702/34

(58) Field of Classification Search ..................... 702/34  
See application file for complete search history.

(56) References Cited

OTHER PUBLICATIONS

H. Liu, Effect of a biasing electric field on the propagation of antisymmetric Lamb waves in piezoelectric plates, International Journal of Solids and Structures 39 (2002) 1777-1790, 2002 Elsevier Science Ltd.*

* cited by examiner

*Primary Examiner* — Tung S Lau  
(74) *Attorney, Agent, or Firm* — Innovation Counsel LLP

(57) ABSTRACT

A method useful in structural health monitoring (SHM) systems for detecting damages in metal structures includes extracting the zero-order symmetric and anti-symmetric mode signal components from each of a plurality of current sensor signals of an array of transducers mounted on the structure, matching the extracted signal components with corresponding signal components of a plurality of baseline sensor signals previously detected in the structure, computing respective indices $I_{S0}$ and $I_{A0}$ for each of the matched extracted current and baseline signal components based on respective signal energies thereof, and determining the presence of a damage in the structure if either of the indices $I_{S0}$ and $I_{A0}$ of a plurality of neighboring sensor paths of the structure is greater than a selected threshold value.

9 Claims, 3 Drawing Sheets

DETECTING DAMAGE IN METAL STRUCTURES WITH STRUCTURAL HEALTH MONITORING SYSTEMS

RELATED APPLICATIONS

This application claims the benefit of U.S. Provisional Patent Application No. 60/912,112, entitled "Structural Health Monitoring System And Methods For Use," filed Apr. 16, 2007, the entire disclosure of which is incorporated herein by reference.

BRIEF DESCRIPTION OF THE INVENTION

This invention relates generally to the field of Structural Health Monitoring (SHM). More specifically, this invention relates to methods for detecting damage in metal structures with SHM systems.

BACKGROUND

In recent years, SHM technologies have received increasing attention by industry as a potential method for improving the safety and reliability of structures and thereby reducing their operational cost. SHM is perceived as a revolutionary method for determining the integrity of structures involving the use of multidisciplinary fields, including sensors, materials, structure mechanics, signal processing and interpretation, and system integration. One thrust of this technology is the development of self-sufficient SHM systems for the continuous monitoring, inspection and damage detection of structures with minimal labor involvement. The aim of the technology is not simply to detect structural failures, but also to provide an early indication of physical damage that might give rise thereto. The early warning provided by a SHM system can then be used to define remedial strategies before the structural damage leads to failure. However, to ensure the reliability and robustness of SHM technologies for use in real-world applications, efficient design methodologies and implementation procedures are needed.

There are unique challenges in SHM which depend on the structural material and geometry, and the types of damages that are to be detected and monitored. In ultrasound Lamb wave based SHM, because of the dispersion characteristics, different wave packets in the received signals are sensitive to different types of damages, depending on the structure material. For example, in composite structures, impact damages could result in the largest change in the zero-order symmetric Lamb wave mode. This mode could be generally sufficient for impact damage detection in composite structures. This is different from metallic structures, where a crack damage could mostly alter the anti-symmetric Lamb wave mode while a corrosion damage could also alter the symmetric mode in the same time. In order to detect damage most effectively and to reduce false-acceptance rate, different wave modes should be used for different materials and problems. Therefore, a need exists to develop different damage detection methods for different applications.

SUMMARY

In accordance with the present disclosure, SHM methodologies are provided for damage detection in metal structures using, for example, ultrasound PZT transducer networks. These novel methodologies are provided in the form of functional "modules" seamlessly integrated into a SHM system. The received sensor signals of the transducer networks are first gated so that the crosstalks are removed using the method described in commonly owned U.S. patent application Ser. No. 12/049,061 by B. Liu et al., incorporated herein by reference.

In one example embodiment, a method useful for detecting damage in a metal structure comprises: Determining featured signal windows of selected signal components for each of a plurality of sensor signals of an array of transducers mounted on the structure; extracting selected signal components from each of a plurality of current sensor signals of the transducer array using the featured signal windows; matching the extracted signal components with corresponding signal components of a plurality of baseline sensor signals previously detected in the structure with the transducer array; computing respective indices $I_{S0}$ and $I_{A0}$ for each of the matched extracted current and baseline signal components based on respective signal energies thereof; and, determining the presence of a damage in the structure if either of the indices $I_{S0}$ and $I_{A0}$ of a plurality of neighboring sensor paths of the structure is greater than selected threshold values of $I_{S0}$ and $I_{A0}$.

In another example embodiment, a method for extracting the respective first arrivals of the zero-order symmetric and anti-symmetric modes and the respective scattering wave packets corresponding thereto from a plurality of sensor output signals of a structural health monitoring (SHM) system comprises: Selecting a set of sensor signals having the same frequency and about the same path length; locally shifting the signals to align their respective phases; computing the average of the signals, the envelope of the average, and the local maxima of the envelope; finding the time locations of the first two local maxima respectively corresponding to the zero-order symmetric and anti-symmetric modes that are greater than a selected threshold; computing the group velocities corresponding to the two modes using their local maximum locations in time and the average path length of the paths of the selected signals; determining the propagation time of the respective first arrival wave packet of each mode of other signals outside the selected set of signals using the computed group velocity of each mode and the path lengths; determining the featured signal windows; and, extracting the first arrival wave packet of each mode and the scattering wave packets respectively corresponding thereto for all of the signals.

A better understanding of the above and many other features and advantages of the novel SHM methods and apparatus for detecting damage in metal structures of the present disclosure may be obtained from a consideration of the detailed description of some example embodiments thereof below, particularly if such consideration is made in conjunction with the several views of the appended drawings, wherein like elements are referred to by like reference numerals throughout.

DETAILED DESCRIPTION

There are many characteristics of a SHM system that are desirable to its practical implementation and use in real world monitoring applications, such as:

High accuracy and reliability;

Low false acceptance and false rejection damage detection rates;

Ease of use, including straightforward sensor array design and installation with minimal training;

Automatic system setup;

Automatic system calibration procedures;

Ability to compensate for environmental changes;

Built-in sensor self-diagnostics.

Figure 1:
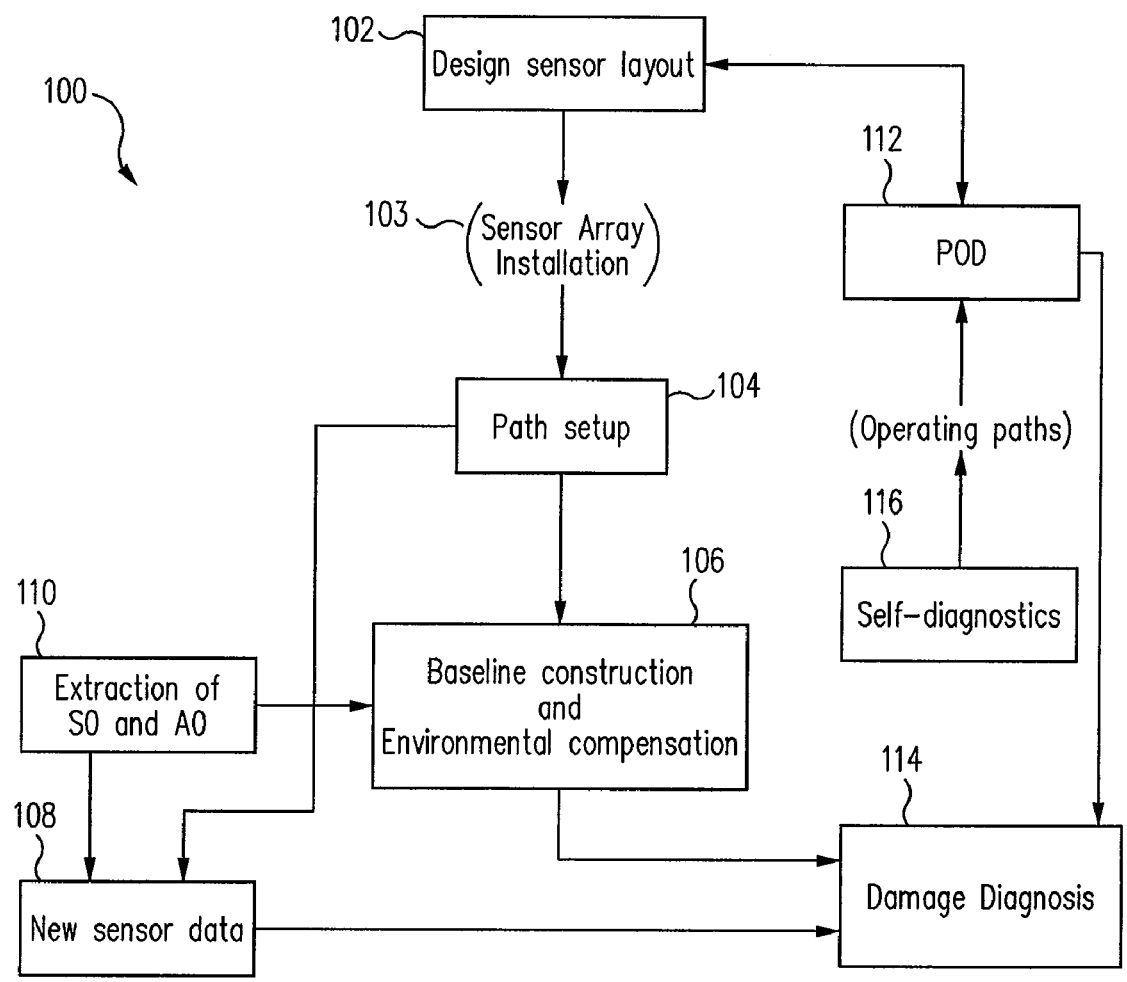
FIG. 1 is a functional block diagram and process flowchart of an example embodiment of a SHM system adapted to detect damage in a metal structure in accordance with the present disclosure.

FIG. 1 is a functional block diagram and process flowchart of an example embodiment of an SHM system 100 adapted to detect damage in a metal structure in accordance with the present disclosure, which provides an efficient way to achieve the above desired SHM system characteristics. The particular example SHM system illustrated comprises seven functional "modules" described in more detail below, including a module 102 for deriving a CAD-designed sensor array 103 that may be implemented in accordance with the techniques described in commonly owned U.S. patent application Ser. No. 12/061,494 by S. Beard, et al., incorporated herein by reference, which uses critical damage size and structural mechanical constraints, such as openings in the structure, as design inputs.

The sensor array 103 may comprise a plurality of transducers, e.g., piezoelectric transducers, such as lead-zirconium-titanate (PZT) transducers, which are capable of reversible operation, i.e., of operating both as an "actuator," i.e., as a device for coupling mechanical wave signals into the monitored structure (not illustrated) in response to the application of a corresponding electrical signal, and as a sensor for sensing wave signals coupled into the structure by other transducers of the array and for outputting an electrical signal corresponding to the wave signal sensed. The respective paths followed by the wave signals between the actuator and sensor transducers of an associated pair of transducers are referred to as propagation, or sensor paths. Damage to the structure, such as a crack intersecting or close to one or more sensor paths, modulates the wave signals traveling along the affected paths in specific ways, and by analyzing the signals sensed, information about the damage, such as its location, can be derived therefrom.

The example system 100 of FIG. 1 may itself automatically setup (functional block 104) the data collection parameters for each actuator-sensor path of the system, including automatic gain and frequency selection, as described in commonly owned U.S. patent application Ser. No. 12/103,562, by Z. Yu et al., incorporated herein by reference. The setup may include the establishment of a baseline set of sensor data for the structure that can be used later during structure monitoring and damage detection as a basis for comparison.

Functional module 106 of the system carries out dynamic baseline data set construction and environment calibration using, for example, the statistical methods described in commonly owned U.S. patent application Ser. No. 12/104,354, by B. Liu et al., incorporated herein by reference. When new sensor data comes into the system 100 from the sensor array 103, functional module 114 compares this data with the baseline data set and then diagnoses structural damage and creates an image of the damage that can be printed out or visually displayed on a display (not illustrated) of the system.

As described in more detail below, functional module 110 of the system extracts the zero-order symmetric and anti-symmetric modes of a sensor signal, and plays the role of signal feature extraction in processing the baseline data and the new sensor data.

Functional modules 112 and 114 include a database and a method for creating the probability of detection (POD) of damage in the monitored structure, and may utilize, for example, the methods and apparatus of commonly owned U.S. patent application Ser. No. 12/103,584, by B. Liu, incorporated herein by reference. While the POD module 112 is a stand-alone component of the system 100, it is desirable for successful structural damage detection, overall performance of the entire system, and the realization of many of the desirable SHM system characteristics described above.

Functional module 116 is also a stand-alone component of the system 100 and performs self-diagnosis of the network sensors. It may, for example, utilize the methods taught in commonly owned U.S. patent application Ser No. 12/039,600, by S. Beard et al., incorporated herein by reference. This module plays a major role in ensuring system reliability.

This disclosure focuses primarily on the implementation and operation of functional modules 110 and 114, i.e., the signal feature extractor module and the sensor data comparator and damage diagnostician module, as well as their complementary interaction with the other functional modules of the system described above.

Featured Signal Window Determination

It has been observed in many SHM studies that, depending on the actuation signal frequency, damages disposed at different locations in a monitored metal structure, and having different sizes, affect the propagating wave signal in different ways. Specifically, when the damage size is relatively small, it may change only a portion of one mode of the signal. Conversely, environmental effects, especially temperature, often change a wave signal over the entire length of the signal. This difference in effects gives rise to a method for reliably detecting damages in a metal structure, and accordingly, accurate extraction of only the damage-sensitive segment(s) of the signal becomes very important for increasing the signal-to-noise ratio and improving the reliability of the SHM system.

In the example embodiments of the present disclosure, the "first arrivals" of the zero-order symmetric and anti-symmetric modes of a detected sensor signal are extracted. Then, for each mode of the signal, the first arrival and the wave packet immediately following the first arrival (i.e., the scattering wave packet) are used as the "featured," i.e., the most relevant signal components for purposes of metal structure damage detection. For each mode of each sensor path, the output of this module is essentially the starting and ending time of a time window that includes the respective first arrival and scattering wave packets. In most situations, this time window is mainly dependent on the actuator-sensor distance, the actuation frequency, and the structure material and geometry, and does not vary significantly with time and environmental conditions. Therefore, the determination of the relevant time windows needs to be done only once using one set of baseline data after the transducers are initially installed on the structure. Thereafter, in future damage detection scenarios, the time windows determined for each mode are applied to the respective sensor path signals of the new current data, which then produce the featured component of each mode for each sensor signal path.

Figure 2:
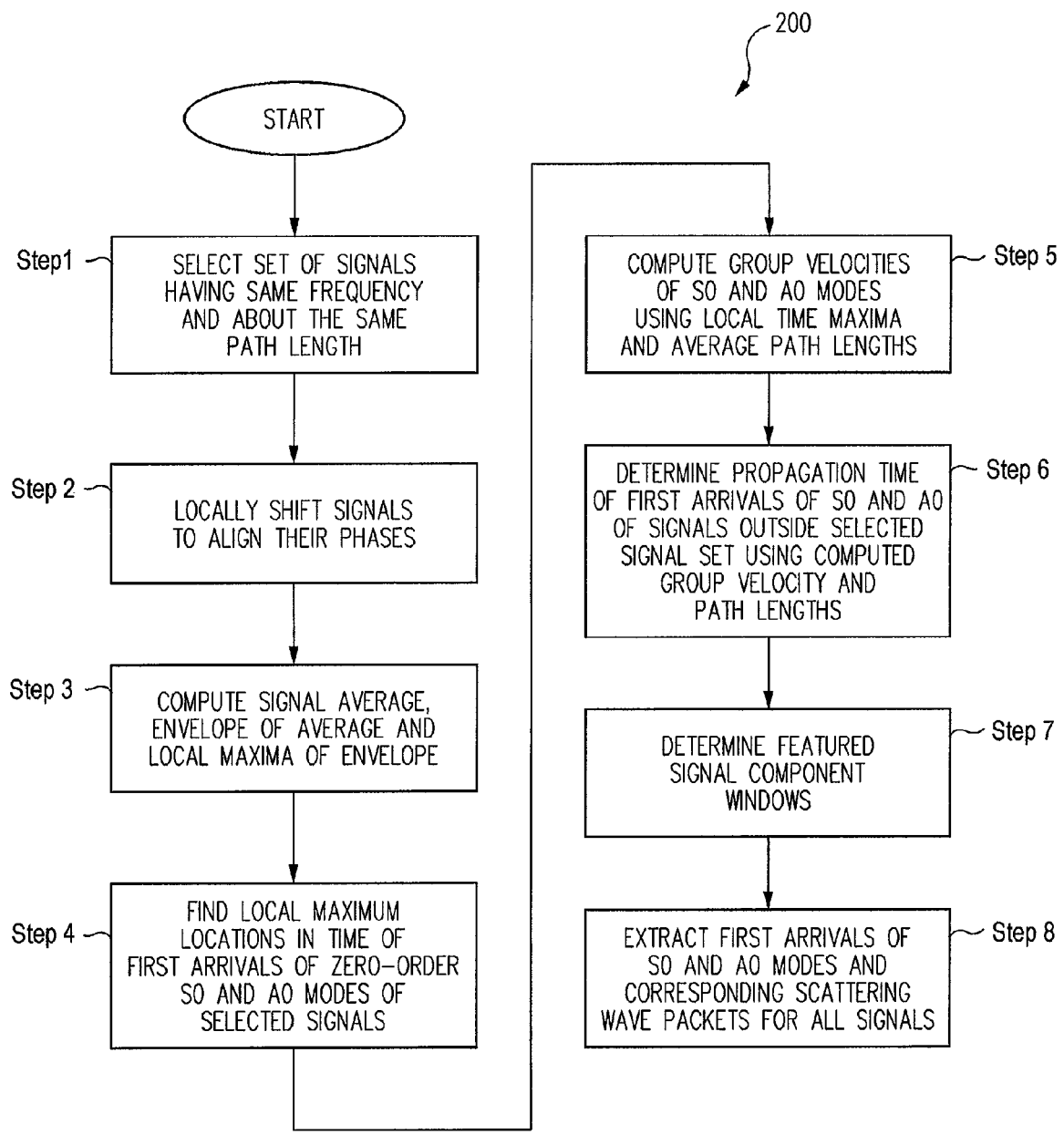
FIG. 2 is a process flow diagram of an example embodiment of a method for extracting the respective first arrivals and corresponding scattering waves of the zero-order symmetric and anti-symmetric modes of a plurality of sensor signals in accordance with this disclosure; and, FIG. 3 is a process flow diagram of an example embodiment of a method for detecting damages in a metal structure in accordance with the present disclosure.

FIG. 2 is a process flow diagram of an example embodiment of a method 200 for extracting the first arrival of different modes and corresponding scattering wave packets of sensor output signals in accordance with the present disclosure. With reference to FIG. 2, the example method comprises:

Step 1: Selecting a set of sensor signals having the same frequency and about the same path length;

Step 2: Locally shifting the signals to align their phases;

Step 3: Computing the average of the signals, the envelope of the average and the local maxima of the envelope. (After the signals are averaged, most of the scattering signal components are cancelled out, since different transducers and signal paths have different scattering and boundary conditions. Conversely, the first arrival wave packet of each mode is substantially retained);

Step 4: Finding the locations in time of the local maxima that are greater than a selected threshold, wherein the first local maximum (i.e., the first in time) is deemed to correspond to the location in time of the first arrival of the zero-order symmetric mode S0, and the second local maximum (i.e., the second in time) is deemed to correspond to the location in time of the first arrival of the zero-order anti-symmetric mode A0. (The selected threshold can be determined empirically, but after the averaging in Step 3 above, the first arrival wave packet of each mode can usually be easily identified.)

Step 5: Computing the group velocities corresponding to the two modes using their respective local maximum locations in time and the average path length of the paths of the selected signals;

Step 6: Determining the propagation time of the respective first arrival wave packet of each mode of other signals outside of the selected set of signals using the computed group velocity of each mode and the path lengths;

Step 7: Determining the featured signal windows; and,

Step 8: Extracting the first arrival wave packet of each mode and the scattering wave packets respectively corresponding thereto for all the signals.

In Step 2 above, the shifting of the signals for phase alignment may be carried out, for example, in accordance with the methods described in commonly owned U.S. patent application Ser. No. 12/104,354, by B. Liu et al. above.

Step 7 above may be carried out, for example, in accordance with the methods described in U.S. patent application Ser. No. 12/049,061 by B. Liu et al. above. More specifically, after the propagation time of the first arrival wave packet of each mode is obtained for each path in Step 6, a local maximum of the signal envelope, $Y_{max}$ can then be located at or close to the time $t_{max}$ that is the propagation time plus the time of the maximum of the actuation signal envelope. Based on the width characteristics of the actuation signals, a threshold window of time width THwin is specified. The starting and ending time of the first arrival wave packet can then be determined. More specifically, let Y be the value of the envelope of the received signal at some time t. Starting from the local maximum $Y_{max}$ mentioned above, the value of Y is decreased gradually. Let t1 and t2 be the time instants at which the envelope value equals Y and t1 and t2 are the closest time to $t_{max}$ from its left and right sides. Then, when t2-t1 equals THwin, the value of t1 and t2 are specified as the starting and ending time of the first arrival wave packet. The scattering wave packet is selected simply as the wave packet immediately following the first arrival wave packet.

Damage Detection

Figure 3:
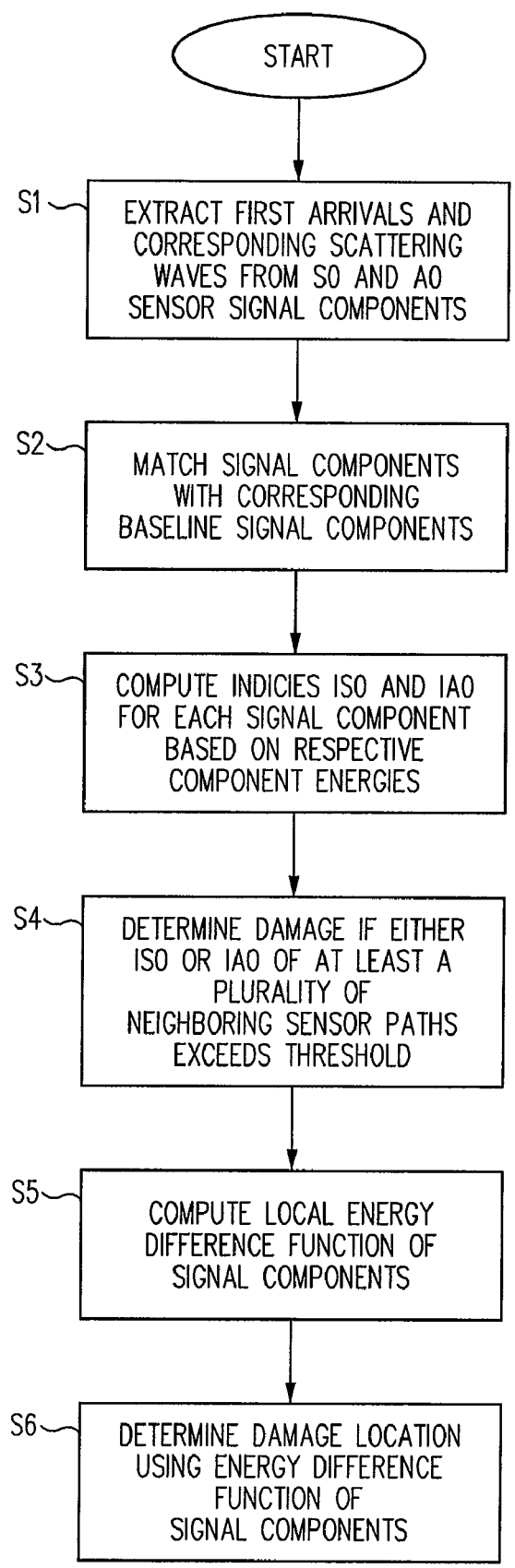

FIG. 3 is a process flow diagram of an example embodiment of a method 300 for detecting damages in a metal structure in accordance with the present disclosure.

With reference to FIG. 3, after the featured signal components of the new signal are extracted at S1 using the example method 200 described above, a "flexible matching method," such as that described in the commonly owned U.S. patent application Ser. No. 12/104,354, by B. Liu et al. above, is first applied to the new signal with respect to the baseline signal at S2. Then, at S3, the indices, $I_{S0}$ and $I_{A0}$, respectively given by equations (1) and (2) below, are computed and used for damage detection:

$$I_{S0} = \sqrt{\frac{|e_c^{S0} - e_b^{S0}|}{e_c^{S0} + e_b^{S0}}} \quad (1)$$

$$I_{A0} = \sqrt{\frac{|e_c^{A0} - e_b^{A0}|}{e_c^{A0} + e_b^{A0}}}, \quad (2)$$

where $e_b^{S0}$ is the energy of the featured component of the baseline signal corresponding to the zero-order symmetric mode S0, and $e_c^{S0}$ is the corresponding featured component of the new signal data, respectively. Similar notations are used in equation (2) above with respect to the zero-order anti-symmetric mode A0.

At S4, if either of $I_{S0}$ and $I_{A0}$ of at least a specified number (e.g., 2 or 3) of neighboring paths is greater than a given threshold value, then damage is deemed to be present in the structure. The threshold value may be determined using, for example, the "outlier detection method" described in commonly owned U.S Pat. application Ser. No. 12/104,354, by B. Liu et al. above.

In order to determine the location of the damage in the structure, a moving window g(t) (e.g., a Gaussian function having the same length as the actuation signal) is first applied to the respective featured components of S0 and A0 of the current and baseline signals. The featured component of the current signal may be denoted by $x_c(t)$, and the featured component of the baseline signal may be denoted by $x_b(t)$. Then, the respective local energies thereof are determined, as defined by the following equations (3) and (4):

$$E_c = \int \{x_c(t)g(t)\}^2 dt \quad (3)$$

$$E_b = \int \{x_b(t)g(t)\}^2 dt, \quad (4)$$

and, at S5, the local energy difference function thereof, as defined by equation (5) below, is computed:

$$I(t) = \frac{|E_c(t) - E_b(t)|}{E_c(t) + E_b(t)}. \quad (5)$$

The local energy difference function of equation (5) is computed for both of the zero-order symmetric mode S0 and anti-symmetric mode A0 of each of the baseline and current signals. Then, at S6, and using this energy function definition, a diagnostic imaging method, such as that described in C. H. Wang, et al., *A Synthetic Time-reversal Imaging Method for Structural Health Monitoring*, 13 Smart Materials and Structures, 415-423 (2004), incorporated herein by reference, can then be used to detect the location of the damage in the structure. More specifically, let it be supposed that a total of N transducers are used in the SHM system, located at $(x_i, y_i)$, $i=1, 2, \ldots, N$, respectively. Let the zero-order symmetric mode local energy difference function of the signal path from sensor i to j be denoted by $I_{ij}^{S0}(t)$, and that of the anti-symmetric mode be denoted by $I_{ij}^{A0}(t)$. Then, the intensity at pixel (x, y) of the diagnostic image of the zero-order symmetric mode is defined as:

$$S^{S0}(x, y) = \sum_{i=1}^{N} \sum_{j=1}^{N} I_{ij}^{S0}\left(\frac{R_i + R_j}{c_g^{S0}}\right), \quad (6)$$

where $R_i$ is the distance between the pixel (x, y) and the location of sensor i $(x_i, y_i)$, $R_j$ is the distance between the pixel (x, y) and the location of sensor j $(x_j, y_j)$, and $c_g^{S0}$ is the group velocity of the zero-order symmetric mode. Similarly, the intensity at pixel (x, y) of the diagnostic image of the zero-order anti-symmetric mode is defined as:

$$S^{A0}(x, y) = \sum_{i=1}^{N} \sum_{j=1}^{N} I_{ij}^{A0}\left(\frac{R_i + R_j}{c_g^{A0}}\right), \quad (7)$$

where $c_g^{A0}$ is the group velocity of the zero-order anti-symmetric mode.

The foregoing process will generate two diagnostic images corresponding to the symmetric and anti-symmetric modes respectively. In each image, the location(s) of the local maximum (or local maxima for multiple damages), will show the location of the damage(s). In the case where the two images show different damage locations, these damages may comprise different types of damages.

It should be noted that the example method 300 described herein differs from that of the above reference in three important aspects: 1) The instant method uses an algorithm to automatically detect the featured components as described above; 2) a local energy difference (i.e., Eq. (5) above) is used instead of the energy or amplitude of the scattered signal to generate the diagnostic images, as taught in the method of the above reference; and, 3) the instant method uses both S0 and A0 modes of signal components for the damage detection. The second difference renders the present method much less sensitive to temperature change.

Damage Detection with a Reduced Number of Sensors

In the situation in which a damaged sensor is detected by the system 100 using a sensor diagnostic method, such as that described in the commonly owned U.S. patent application Ser. No. 12/039,600, by S. Beard, et al. above, the system will automatically re-evaluate the damage detection capability of the sensor array 102 in the region around the damaged sensor. Specifically, it may use the probability of detection (POD) generation method of commonly owned U.S. patent application Ser. No. 12/103,584, by B. Liu above to re-compute the local POD of this region. The damage detection capability in this region of the sensor array will, of course, be reduced due to the presence of the damaged sensor. However, the methods described above may still be used to find damage since the instant methods use a scheme of "single path supposition."

Although the methods and apparatus of the present invention have been described and illustrated herein with reference to certain specific example embodiments thereof, it should be understood by those of skill in this art that a wide variety of modifications and variations may be made to them without departing from the spirit and scope of the invention, as defined by the claims appended hereafter and their functional equivalents.

What is claimed is:

1. A method for detecting damages in a metal structure, the method comprising:

receiving a plurality of sensor signals from an array of sensors mounted on a structure;

determining featured signal windows of selected signal components for each of the plurality of sensor signals of the array of sensors mounted on the structure;

extracting selected signal components from each of a plurality of current sensor signals of the sensor array using the featured signal windows;

matching the extracted signal components with corresponding signal components of a plurality of baseline sensor signals previously detected in the structure with the sensor array;

computing respective indices $I_{S0}$ and $I_{A0}$ for each of the matched extracted current and baseline signal components based on the respective signal energies thereof; and, determining the presence of a damage in the structure if either of the indices $I_{S0}$ and $I_{A0}$ of at least a specified number of neighboring sensor paths of the structure is greater than selected threshold values of $I_{S0}$ and $I_{A0}$.

2. The method of claim 1, wherein the selected signal components comprise the respective first arrival wave packets of the zero-order symmetric and anti-symmetric modes S0 and A0 of the signals and the respective scattering wave packets corresponding thereto.

3. The method of claim 1, wherein the determining of the featured signal windows comprises:

selecting a set of sensor signals having the same frequency and about the same path length;

locally shifting the signals to align their respective phases;

computing the average of the signals, the envelope of the average, and the local maxima of the envelope;

finding the time locations of the first two local maxima respectively corresponding to the zero-order symmetric and anti-symmetric modes that are greater than a selected threshold;

computing the group velocities corresponding to the two modes using their local maximum locations in time and the average path length of the paths of the selected signals;

determining the propagation time of the respective first arrival wave packet of each mode of other signals outside the selected set of signals using the computed group velocity of each mode and the path lengths;

determining the featured signal windows; and, extracting the first arrival wave packet of each mode for all the signals and the scattering wave packets respectively corresponding thereto.

4. The method of claim 1, wherein the indices $I_{S0}$ and $I_{A0}$ are respectively determined according to the equations:

$$I_{S0} = \sqrt{\frac{|e_c^{S0} - e_b^{S0}|}{e_c^{S0} + e_b^{S0}}} \text{ and } I_{A0} = \sqrt{\frac{|e_c^{A0} - e_b^{A0}|}{e_c^{A0} + e_b^{A0}}},$$

wherein $e_b^{S0}$ and $e_c^{S0}$ are the energies of the respective selected components of baseline and current signal data corresponding to the respective zero-order symmetric modes thereof, and $e_b^{A0}$ and $e_c^{A0}$ are the energies of the respective selected components of baseline and current signal data corresponding to the respective zero-order anti-symmetric modes thereof.

5. The method of claim 1, further comprising:

computing local energy difference functions I(t) of the selected components of the S0 and A0 modes of each of the current and baseline sensor signals; and, determining the location of the damage in the structure with a diagnostic imaging method using the computed local energy difference functions of the signal components.

6. The method of claim 5, wherein the computing of the local energy difference functions I(t) of the selected components comprises:

applying a moving window function g(t) to each of the respective selected components of each of the current and baseline signals; and, computing the respective local energies $E_c$ and $E_b$ of each of the selected components of each of the current and baseline signals.

7. The method of claim 6, wherein the moving window function g(t) comprises a Gaussian function having the same length as an actuation signal used to produce the current sensor signals.

8. The method of claim 6, wherein the respective selected components of the current signals are denoted by $x_c(t)$ and the selected component of the baseline signal is denoted by $x_b(t)$, and wherein the computing of the respective local energies $E_c$ and $E_b$ of each of the selected components comprises evaluating the equations:

$$E_c = \int \{x_c(t)g(t)\}^2 dt \text{ and } E_b = \int \{x_b(t)g(t)\}^2 dt$$

for each of the current and baseline signals.

9. The method of claim 8, wherein the computing of the local energy difference function I(t) of the respective selected components of the signals comprises evaluating the equation:

$$I(t) = \frac{|E_c(t) - E_b(t)|}{E_c(t) + E_b(t)}$$

for each of the current and baseline signals and for both the zero-order symmetric and anti-symmetric modes.

* * * * *